United States Patent
He et al.

(10) Patent No.: US 7,122,081 B2
(45) Date of Patent: Oct. 17, 2006

(54) PROCESS FOR AQUEOUS MILLING OF QUINACRIDONE PIGMENTS

(75) Inventors: Yingxia He, Wilmington, DE (US); Colin D. Campbell, Claymont, DE (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/988,250

(22) Filed: Nov. 12, 2004

(65) Prior Publication Data

US 2005/0187313 A1 Aug. 25, 2005

Related U.S. Application Data

(60) Provisional application No. 60/519,842, filed on Nov. 13, 2003.

(51) Int. Cl.
- *C09B 48/00* (2006.01)
- *C09B 67/20* (2006.01)
- *C09B 67/52* (2006.01)

(52) U.S. Cl. .................. 106/493; 106/410; 106/411; 106/412; 106/413; 106/494; 106/495; 106/496; 106/497; 106/498; 106/499; 524/90; 546/49

(58) Field of Classification Search ............... 106/410, 106/411, 412, 413, 493, 494, 495, 496, 497, 106/498, 499, 31.77; 524/90; 546/49
See application file for complete search history.

(56) References Cited

U.S. PATENT DOCUMENTS

| | | | |
|---|---|---|---|
| 2,402,167 A | 6/1946 | Lang et al. | 260/314.5 |
| 2,816,115 A | 12/1957 | Howell | 260/314.5 |
| 3,030,370 A | 4/1962 | Jackson | 260/279 |
| 3,326,918 A | 6/1967 | West | 260/279 |
| 3,607,336 A | 9/1971 | Jaffe | 106/288 |
| 4,293,475 A | 10/1981 | Sidi | 260/29.6 |
| 4,455,173 A | 6/1984 | Jaffe | 106/288 |
| 4,597,794 A | 7/1986 | Ohta et al. | 106/20 |
| 4,857,646 A * | 8/1989 | Jaffe | 546/49 |
| 5,084,100 A | 1/1992 | Bauman | 106/495 |
| 5,231,131 A | 7/1993 | Chu et al. | 524/504 |
| 5,383,966 A * | 1/1995 | Johnson | 106/495 |
| 5,432,036 A | 7/1995 | Beach et al. | 430/115 |
| 5,514,510 A | 5/1996 | Hayakawa | 430/108 |
| 5,530,043 A | 6/1996 | Zawacky et al. | 524/317 |
| 5,840,901 A | 11/1998 | Bäbler | 549/49 |
| 5,955,232 A | 9/1999 | Little et al. | 430/106 |
| 6,056,814 A | 5/2000 | Kato et al. | 106/412 |
| 6,210,474 B1 | 4/2001 | Romano, Jr. et al. | 106/31.6 |
| 6,410,619 B1 | 6/2002 | Green et al. | 524/88 |
| 6,503,317 B1 * | 1/2003 | Ortalano et al. | 106/493 |
| 6,916,862 B1 * | 7/2005 | Ota et al. | 523/200 |

OTHER PUBLICATIONS

English language abstract for JP 55089366 (Jul. 1980).
R. B. McKay, JOCCA, "Control of the Application Performance of Classical Organic Pigments", pp. 89-93, (1989) (no month).

\* cited by examiner

*Primary Examiner*—Anthony J. Green
(74) *Attorney, Agent, or Firm*—Shiela A. Loggins

(57) ABSTRACT

The present invention is directed to an aqueous process for reducing particle size of organic pigments by milling the crude pigment in the presence of a water soluble styrene copolymer dispersant, optionally a defoamer, optionally an additive, and greater than about 10 wt. % water, and isolating the organic pigment.

23 Claims, No Drawings

PROCESS FOR AQUEOUS MILLING OF QUINACRIDONE PIGMENTS

This application claims the benefit of U.S. Provisional application No. 60/519,842, filed Nov. 13, 2003.

BACKGROUND OF THE INVENTION

The present invention is directed to an aqueous process for reducing particle size of organic pigments by milling the crude pigment in the presence of styrene copolymer dispersants.

It is well known in the art that organic pigments, such as quinacridones, as synthesized, are generally unsuitable for use as pigments and must be further processed to develop the requisite pigmentary properties such as particle size, particle shape, polymorphic phase, and tinctorial strength.

In order to obtain the color properties required for a particular application, the pigment crude must be converted to a pigmentary grade with a proper tint strength, transparency or opacity for a particular application. The effectiveness of a given pigment type in imparting color is dependent upon it's particle size in dispersion. Thus, color strength, transparency and opacity are all properties that are highly dependant on particle size. Consequently, crude organic pigments undergo one or more finishing or conditioning steps that require particle size reduction. See, for example R. B. McKay, "Control of the Application Performance of Classical Organic Pigments" in JOCCA, 89–93.

For example, quinacridone can be synthesized by a peroxide process, as described in U.S. Pat. No. 5,840,901. The obtained pigment is called a pigment crude because the pigment does not have the color property needed for various applications. Further size reduction is necessary. There are many traditional ways of achieving proper pigment particle size including dry milling processes, such as those published in U.S. Pat. Nos. 2,402,167, 3,030,370 and 5,084,100. These references disclose pigment particle size reduction by milling dry pigment powder in the presence of large amounts of inorganic salt and metal nails and/or balls. In this process, pigment crude is first milled to an almost amorphous phase, followed by a re-growth process in order to achieve the proper crystal size. This milling of pigment crude followed by the re-crystallization makes this finishing process complicated and costly. Another traditional pigment finishing process is acid drowning, as described in, for example, U.S. Pat. Nos. 3,326,918, 3,607,336 and 4,455,173. In this process, crude organic pigment is dissolved in a strong acid such as sulphuric acid, often in the presence of polar organic solvent. Then the pigment is drowned out and re-crystallized into an appropriate particle size designed for a particular application. In both processes, the initially synthesized pigment crystal is more or less destroyed then rebuilt, adding significant cost to the final product. Further, the dry milling process requires the presence of inorganic salts and re-crystallization in strong acid, generating significant environmental waste. The dissolution process similarly generates large quantities of waste acid.

Milling methods are known for improving properties of various organic pigments. Some examples are in U.S. Pat. Nos. 6,210,474, 4,597,794, 5,231,131 and 5,530,043. However, the milled pigment in these patents is not the crude organic pigment but a finished pigment. Additionally, the dispersing milling agent is not a styrene copolymer.

U.S. Pat. No. 6,410,619 describes a method for conditioning of crude organic pigments using pure acrylic copolymer dispersants. Styrene copolymer is disclosed in EP 496 149 in making aqueous emulsions for use in graphics. JP 55089366 and U.S. Pat. No. 4,293,475 disclose styrene copolymers for making pigment dispersions. Patents WO9905575, EP 636,942 and U.S. Pat. No. 5,432,036 disclose styrenic polymer based resins for making toner compositions for dry electro-photoconductive imaging. U.S. Pat. No. 2,816,115 describes the use of a hydrolysed styrene-maleic anhydride copolymer for dispersing crude phthalocyanine pigments. U.S. Pat. No. 6,056,814 describes the use of a styrene copolymer for dry milling a crude organic pigment.

There is a need for a process that reduces particle size but does not destroy the crystal structure of the pigment and that can be used for both particle size reduction of beta and gamma crystal phases. There is also a need for an environmentally sound process that does not produce large amounts of waste in the milling or recrystallization. Additionally there is a need for a process that allows the reduction in particle size at high pigment loadings thus increasing the manufacturing through-put. Further, there is need for a process that does not require the crude pigment to be dried, a considerable energy cost savings, before reducing particle size. Accordingly, the process of the instant invention has all of the above advantages.

None of the above references disclose the use of a styrene copolymer dispersant as an aqueous milling agent for the purposes of reducing particle size to the nanometer range to improve the optical properties of a crude organic pigment.

SUMMARY OF THE INVENTION

The present invention relates to an aqueous particle size reduction process of quinacridone pigments using medium to high molecular weight styrene copolymer as dispersant. The products obtained optionally may be ripened under basic or acid conditions to re-grow crystals in the presence of the styrene copolymer dispersant. Thus the inventive process avoids the need for finishing and milling processes requiring the use of strong acids and/or milling with inorganic salts.

The aqueous organic pigment particle size reduction process disclosed in this invention is an economic process in comparison with known methods. This process is the first in the art to use styrene copolymer dispersants for aqueous particle size reduction of crude organic pigment to the nanometer range. The products obtained, with or without further ripening, have excellent application properties in coatings, films, plastics and inks. The product obtained also has exceptional dispersibility and light stability. This simple milling process can be used to produce transparent or semi-transparent pigment products in combination with milling, and particle size re-growth process suitable for production of high performance opaque pigments.

The isolated milled organic pigment or pigment mixtures are preferably re-grown under basic conditions to form an opaque pigment.

The pigment of the invention may be isolated and dried in pure form, in which case it is readily dispersible thereafter in plastics, paints and printing inks using, for example, a ball mill or bead mill. As a moist presscake, it can also be used directly to prepare pigment dispersions for inks, coatings and cosmetics.

The pigments made by the process of the invention (with optional further additives) can also be added to a polymer in the form of a masterbatch ("concentrate") which contains the components in a concentration of, for example, about 1% to about 40% and preferably 2% to about 20% by weight incorporated in a polymer.

Dispersions of the pigments of the invention are also ideally suited as concentrates for preparing printing inks that have excellent applications properties, especially attractive coloristics with high color strength.

The materials containing the isolated pigments made by the process of the invention described herein can be used for the production of moldings, rotomolded articles, injection molded articles, blow molded articles, films, tapes, monofilaments, fibers, nonwovens, profiles, adhesives or putties, surface coatings and the like.

All weights unless otherwise stated are based on the total weight of the composition or mixture. The weight percent of the water-soluble styrene copolymer dispersant is based on the dry weight of the crude organic pigments.

The instant process for particle size reduction of organic pigments to improve optical properties of said pigments comprises
 (a) milling
 a mixture comprising:
   i.) from about 10 to about 60 wt. % one or more crude organic pigments,
   ii.) from about 0.1 to about 25 wt. % of a water-soluble styrene copolymer dispersant based on the dry weight of the crude organic pigment,
   iii.) optionally from about 0.1 to about 1.0 wt. % of defoamer,
   iv.) optionally from about 0.1 to about 5.0 wt. % of an additive based on the dry weight of the crude organic pigment, and
   v.) greater than about 10 wt. % water, wherein the weights of components i.), iii.) and v.) are based on the total weight of the mixture, and
 (b) isolating the milled organic pigment.
 Preferably, the mixture comprises
   i.) From about 15 to about 35 wt. % one or more crude organic pigments;
   ii.) ii.) from about 1 to about 20 wt. % of a water-soluble styrene copolymer dispersant based on the dry weight of the crude organic pigment;
   iii.) optionally from about 0.1 to about 1.0 wt. % of defoamer,
   iv.) optionally from about 0.5 to about 5.0 wt. % of an additive based on the dry weight of the crude organic pigment,
   and
   v.) greater than about 30 wt. % of water, wherein components i.), iii.) and v.) weights are based on the total weight of the mixture.

In this process, the pigment suspension is continuously circulated through the milling media, such as zirconium oxide beads in a mill such as a Dyno-mill or Netzsch-mill. Pigment primary particle size distribution is reduced to about 30 to about 300 nm depending on the milling time and size of milling media. Preferably the pigment primary particle size distribution is reduced to about 40 to about 200 nm. Optionally, the re-growth process may be followed in order to achieve the opacity needed for a particular application. The products obtained from this invention process can be transparent, semi-transparent or opaque, with excellent properties of color strength, rheology, heat stability and weather durability in paint, plastics or ink applications.

DETAILED DESCRIPTION OF THE INVENTION

Pigment crude used in this invention includes perylenes, quinacridones, phthalocyanines, isoindolines, dioxazines, triphendioxazines, 1,4-diketopyrrolopyrroles, anthrapyrimidines, anthranthrones, flavanthrones, indanthrones, perinones, pyranthrones, thioindigos, 4,4'-diamino-1,1-dianthraquinonyl, and azo compounds, as well as substituted derivatives thereof. Mixtures, including solid solutions, may also be prepared. Preferred organic pigments are the high performance pigments such as perylene, quinacridone, phthalocyanine, isoindoline, 1,4-diketopyrrolopyrroles and dioxazine pigments. Especially preferred pigments are quinacridones, perylenes and 1,4-diketopyrrolopyrroles.

Crude Pigment

The crude pigment or pigment mixtures are generally those lacking in properties required for a colorant because of inferior color development and having a particle diameter size range of about 0.2 to about 40 μm, preferably 0.3 to about 4 μm, most preferably about 1.0 to about 3.0 μm. Alternatively, in the instant invention, commercially available pigments composed of pigment particles with a particle diameter size range of about 0.3 to about 0.5 μm may be used as the raw materials to be milled.

In particular, the substituted and unsubstituted quinacridones of formula (A) in beta and gamma crystal phases are especially preferred.

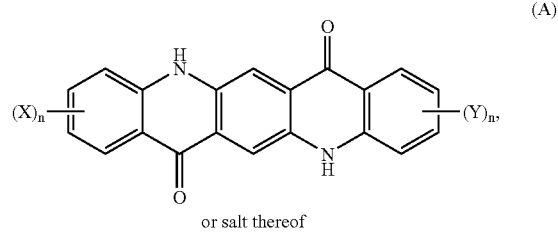

(A)

or salt thereof in which X and Y, independently of one another, are hydrogen, halogen, —OH, —NO$_2$, —CF$_3$, an C$_1$–C$_4$alkyl group, a substituted C$_1$–C$_4$alkyl group, a C$_1$–C$_4$alkoxy group, a substituted C$_1$–C$_4$alkoxy group, a phenyl group, a cyclohexyl group, a phenoxy group, —COOH, a —COO—C$_1$–C$_4$alkyl group, —SO$_3$H, a phenylamino group, a benzamino group, —N(CH$_3$)$_2$, —SO$_2$NH$_2$, —SO$_2$N(CH$_3$)$_2$, a pyridino group, —CONH$_2$ or —CON(CH$_3$)$_2$, especially H, F, Cl, Br, I, C$_1$–C$_4$alkyl, or C$_1$–C$_4$alkoxy, and n is 0, 1, or 2, especially 0, or 1, C$_1$–C$_4$alkoxy group are defined as having up to 4 carbon atoms and is a branched or unbranched radical, for example methoxy, ethoxy, propoxy, isopropoxy, and n-butoxy.

C$_1$–C$_4$alkyl group is difined as having up to 4 carbon atoms and is a a branched or unbranched radical, for example methyl, ethyl, propyl, isopropyl, and n-butyl.

Further preferred quinacridones, such as, for example, quinacridone, 2,9-dichloroquinacridone, 3,10-dichloroquinacridone, 4,11-dichloroquinacridone, 2,3,9,10-tetrachloroquinacridone, 2,4,9,11-tetrachloroquinacridone, 2,9-difluoroquinacridone, 2,9-dibromoquinacridone, 2,9-dimethylquinacridone, 3,10-dimethylquinacridone, 4,11-dimethylquinacridone, 2,4,9,11-tetramethylquinacridone, 2,9-di(tert-butyl)quinacridone, 2,9-dihydroxylquinacridone, 2,9-di(trifluoromethyl)quinacridone, 2,9-dimethoxyquinacridone, 2,9-diethoxyquinacridone, 2,4,9,11-tetramethoxyquinacridone, 2,9-dicarboxylquinacridone, 2,9-dichlorohexylquinacridone, 2,9-diphenylquinacridone, 2,9-di(dimethylamino)quinacridone, 2,9-di(dimethylaminosulfo)quinacridone, 2,9-di(dimethylaminocarbonyl)quinacridone, 3,10-dinitroquinacridone, 2,9-dimethyl-4, 11-dichloroquinacridone, 2,9-dimethyl-4,11-dicarboxyquinacridone, and 2,9-dipyridinoquinacridone. Quinacridones can exist in several polymorphic phases (e.g. alpha, beta, gamma phase). All are encompassed.

The most preferred quinacridone of formula (A) is a beta or gamma unsubstituted quinacridone or 2,9-dichloroquinacridone.

Copolymer Dispersant

As copolymer dispersant for the aqueous milling of the crude pigment, it is preferred to use a copolymer consisting of hydrophilic and hydrophobic functional groups. The former portion can be ionizable and can form ammonium or alkali metal salts. The chemical structure of a typical styrene copolymer dispersant is represented below in formula (B):

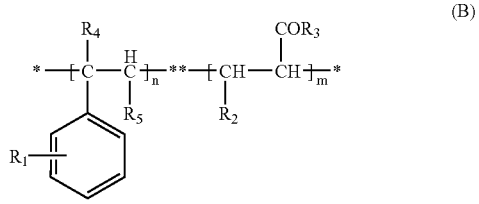

(B)

where $R_1$ is H, $C_1$–$C_4$ alkyl, fluoro, chloro, bromo, iodo, nitro, or amino groups, $C_1$–$C_{18}$ alkylene, or $C_1$–$C_4$ alkoxy groups. $R_2$ is H and $C_1$–$C_4$ alkyl group, $R_3$ is hydroxyl or $C_1$–$C_4$ alkoxy group, and $R_4$ and $R_5$ are, independently of one another, H, or $C_1$–$C_4$ alkyl group. $100>n>1$. $100>m>1$. The percent styrene monomer unit in the copolymer can be in the range of about 10 to about 90 wt. %, although it is preferred that the styrene or styrene derivative monomer makes up greater than about 50% of the total monomer units of the copolymer in formula (B).

The "*" in formula (B) could be an endcapping unit or a terminating group. The "**" connecting the two monomer units is meant to show that the polymer may be random, block or grafted.

The monomer unit or monomer units are derived from the monomer or monomers used in forming the final styrene copolymer.

The preferred styrene copolymer dispersant of the instant invention has a molar ratio of styrene to (meth)acrylic monomer units that is equal to or greater than about 2 to 1 respectively.

The copolymer is preferably a random, block or graft copolymer.

The hydrophilic portion of the copolymer is made from suitable unsaturated acid monomer units including acrylic acid, methacrylic acid, or hydrolysed esters of acrylic or methacrylic acid. Examples of suitable unsaturated acid monomer units include, (meth)acrylic acid and their lower alkyl esters such as methyl methacrylate, ethyl methacrylate, ethyl acrylate, maleic acid, fumaric acid, itaconic acid, citraconic acid, cinnamic acid, crotonic acid, and the like, and combinations thereof. The unsaturated acid monomer unit can also be in the form of a carboxylate salt with a suitable cation including sodium, potassium, and ammonium.

(Meth)acrylic acid refers to acrylic and methacrylic acid derivatives.

The styrene copolymer dispersant comprises a maximum of about 49% (meth)acrylic acid, (meth)acrylic acid derived monomer units or salts thereof, based on the total number monomer units of the copolymer dispersant. It is especially preferred that the unsaturated acid monomer unit is (meth)acrylic acid, a (meth)acrylic acid derivative or a carboxylate salt thereof.

Monomers which form the hydrophobic portion of the copolymers can be selected from styrene and styrene derivatives, such as $C_1$–$C_4$ alkyl or substituted styrene, vinyltoluene, alpha-methylstyrene, o-, p-, and m-chloromethyl styrene, styrene substituted with fluoro, chloro, bromo, iodo, nitro, or amino groups, butadiene, or octadecene. The styrene copolymers used in this invention are medium to high molecular weight copolymers, with an average molecular weight in the range of about 5,000 to 20,000. Preferably the molecular weight of copolymers range from about 9,000 to 17,000.

The preferred styrenic copolymers used in this invention are styrene acrylic copolymer, which are commercially available from many specialty chemical manufacturers, such as SC Johnson Polymer (1525 Howe St.; Racine, Wis. 53403; USA). Examples of products can be all JONCRYL type of styrene copolymers, including solid state product and their solutions, such as ammonium and sodium salts. Molecular weight for these styrene copolymers range from about 8,500 to about 16,500. The ratio of styrene to acrylic monomer units is equal to or greater than about 2 to 1 respectively on a molar basis.

The styrene copolymer makes up about 0.1 to about 25 wt. % of the dry pigment weight in wet milling mixture, preferably about 1 to about 20 wt. % of the pigment weight.

The wet-milling mixture contains about 10 to about 60 wt. % of organic pigment in the total wet milling mixture, preferably about 15 to about 35 wt. %.

The styrene copolymer can be added before and during milling to control the viscosity of the crude pigment milling mixture.

The styrene copolymer is preferably soluble in the aqueous milling media.

Milling

Aqueous milling is carried out using known wet-milling methods. Although the particular milling apparatus is generally not critical, suitable mills include horizontal mills, for example, Dyno-mill, Eiger mills, Netzsch mills, and Super mills. Additional vertical mills, ball mills, attritors, vibratory mills, and the like containing various grinding media are suitable. Suitable grinding media include salt, sand, glass beads, ceramic beads and alumina, or metal beads.

Regardless of the type of mill used, the crude pigment, the styrenic copolymer and the other optional components are milled until the desired particle size is reached. Milling temperature depends on the size of the mill, and the quantity of crude pigment being milled but is generally carried out at a temperature of 0° C. to about 60° C. Preferably the process milling temperature is 15° C. to about 60° C. Optionally, cooling with water can control the temperature.

In the instant invention, the average particle diameter of the resulting aqueously milled pigments are about 30 to about 300 nm, preferably about 40 to about 200 nm.

Time for Grinding

Particle size reduction time may vary from thirty minutes to twelve hours depending upon the particle size needed for a particular application and the particular crude pigment being wet-milled. In the case of beta-quinacridone crude, the milled product maintained beta-crystal phase after 12 hours of aqueous milling. For gamma quinacridone, gamma-II crystal phase completely converted to gamma-I phase after the crude was milled for five hours. The highest tint strength was achieved within five hours milling time. Extension of milling time allowed the pigment to develop transparency, but tint strength stayed constant, or changed only slightly.

Grinding Media

Grinding media is generally loaded to about 75%–85% of chamber space. The milling media, consists of beads composed of materials such as zirconium oxide, glass, borosilicate, metal, alumina and polymeric beads for example, those described in U.S. Pat. Nos. 5,902,711, and 5,478,705.

Milling Liquid

Suitable milling liquid is water, and can include less than 5 wt. % of polar organic solvent, such as dimethylformamide, dimethylacetamide, dimethylsulfoxide, lower aliphatic alcohols such as methanol, ethers including tetrahydrofuran and dioxane, and alkylene glycols and triols such as ethylene glycol and glycerol.

The milling liquid is made up of greater than about 10 wt. % water, preferably greater than about 20 wt. % water, and most preferably greater than 30 wt. % water.

Milling Additives

Colored additives, such as organic pigment derivatives, or uncoloured additives, such as polymers, can also optionally be added to the milling mixture during the milling process.

The crude pigment may be optionally wet-milled with other additives such as surface modification reagents, rheology improving agents, texture improving agents, defoamers, wetting agents, particle growth inhibitors, crystal phase directors and antiflocculants.

Surface modifying reagents, rheology improving agents and texture improving agents may include quinacridone monosulfonic acid or quinacridone monosulfonic acid aluminum salt or 3,5-dimethylpyrazol-1-methyl quinacridone, Other suitable texture improving agents are, in particular, fatty acids of not less than 18 carbon atoms, for example stearic or behenic acid or their amides or metal salts thereof, preferably sodium or ammonium salts, as well as plasticizers, waxes, resin acids such as abietic acid or metal salts thereof, colophonium, alkyl phenols or aliphatic alcohols such as stearyl alcohol or vicinal diols such as dodecane-1, 2-diol. The additives may be added directly to the milling slurry or at the same time as the crude pigment. The additive or additives may optionally be added at about 0.5–20.0 wt. % based on the dry weight of the crude organic pigment. Preferably the additive or additives are optionally added at about 1.0–5.0 wt. % based on the dry weight of the crude organic pigment.

Defoamer

Defoamers can be used optionally in the inventive wet-milling process. Acetylenic based defoamers are preferred. The defoamer may be added before and/or during milling for foam control.

Isolation of Wet-Milled Crude Pigment

After milling, the pigment may be separated from the milling mixture by one or more isolation methods known in the art. Filtration, followed by washing to remove residual salts and solvent, is the preferred separation method. Other collection methods known in the art, such as tray drying, spray drying, spin flash drying, lyophilization, centrifugation, or simple decantation are also suitable isolation methods. Such methods can be used individually or in combination.

The pigments produced by the present method are suitable as coloring matter for inorganic or organic substrates. They are highly suitable for coloring high molecular weight materials, which can be processed to casted and molded articles or which are used in ink and coating compositions such as solvent or water based coatings, for example in automotive coatings. Preferred high molecular weight materials are plastics that are subsequently calendered, cast, molded or processed to fibers and industrial or automotive paints or ink coatings.

For the purposes of the invention, high molecular weight material is defined as material in the range of $10^3$ to $10^8$ g/mol.

Suitable high molecular weight organic materials include thermoplastics, thermoset plastics or elastomers, for example, cellulose ethers; cellulose esters such as ethyl cellulose; linear or crosslinked polyurethanes; linear, crosslinked or unsaturated polyesters; polycarbonates; polyolefins such as polyethylene, polypropylene, polybutylene or poly-4-methylpent-1-ene; polystyrene; polysulfones; polyamides; polycycloamides; polyimides; polyethers; polyether ketones such as polyphenylene oxides; and also poly-p-xylene; polyvinyl halides such as polyvinyl chloride, polyvinylidene chloride, polyvinylidene fluoride or polytetrafluoroethylene; acrylic and methacrylic polymers such as polyacrylates, polymethacrylates or polyacrylonitrile; rubber; silicone polymers; phenol/formaldehyde resins; melamine/formaldehyde resins; urea/formaldehyde resins; epoxy resins; diene rubbers or copolymers thereof such as styrene butadiene rubber; acrylonitrile-butadiene rubber or chloroprene rubber; singly or in mixtures.

Generally, the present reduced size gamma and/or beta quinacridone pigments are used in an effective pigmenting amount, for example, of 0.01 to 30% by weight, preferably 0.1 to 10% by weight, based on the weight of the high molecular weight organic material to be pigmented. Thus, the present invention also relates to a pigmented plastic composition, which comprises a plastic material and an effective pigmenting amount of a pigment or pigment solid solution prepared according to a process of the present invention, and to a process for preparing said pigmented plastic compositions.

The pigments made by the present process are easily dispersible and can be readily incorporated into organic matrixes to provide homogenous colorations possessing high saturation.

The high molecular weight organic materials are pigmented by the pigments made by the process of the invention by mixing the pigments, if desired in the form of a masterbatch, into substrates using high shear techniques including roll mills or a mixing or grinding apparatus. The pigmented material is then brought into the desired final form by known methods, such as calandering, pressing, extruding, brushing, casting or injection molding.

EXAMPLES

The aqueous particle size reduction process is performed using circulation milling media, such as zirconium oxide beads in a Dyno-mill and Netzsch-mill, in a size range of about 0.2 to about 1.2 mm diameter with a loading of about 75 to about 85% of milling chamber space. Other than water, the milling slurry has a composition of about 10 to about 60% organic pigment or mixture of pigments based on the total weight of the mixture, about 0.1 to about 20 wt. % of styrene copolymer dispersant based on the dry weight of the crude pigment and about 0.1 to about 1 wt. % defoamer based on the total weight of the mixture. Optionally, the milling media may have about 0.5–5 wt. % non-pigment milling additive, pigment additive or mixtures of additives based on the dry weight of the crude organic pigment. Particle size reduction time may vary from about thirty minutes to about twelve hours in order to achieve the particle size needed for the application. Milled product may be isolated after particle size reduction process, or the crystal size can be re-grown by heating the aqueous slurry to about 70 to about 95° C. with addition of base, polar organic solvent and/or amine salt.

Color data is obtained using CM-3600d spectrophotometer manufactured by Minolta Corporation USA. 101 Williams Drive, Ramsey, N.J.

The PVC plastic test and engineering plastic HDPE test are explained below.

The PVC Plastic Test 63.0 grams of polyvinyl chloride, 3.0 grams epoxidized soybean oil, 2.0 grams of barium/cadmium heat stabilizer, 32.0 grams dioctyl phthalate and 1.0 gram of the pigment preparation are mixed together in a glass beaker using a stirring rod. The mixture is formed into a soft PVC sheet with a thickness of about 0.4 mm by rolling for 8 minutes on a two roll laboratory mill at a temperature of 160° C., a roller speed of 25 rpm and friction of 1:1.2, by constant folding, removal and feeding.

Engineering Plastic HDPE Test

Five grams of the pigment preparation prepared according to Example 5, 2.65 grams CHIMASORB 944LD (hindered amine light stabilizer), 1.0 gram TINUVIN 328 (benzotriazole UV absorber) and 2.0 grams IRGANOX B-215 Blend (anti-oxidant), all available from Ciba Specialty Chemicals Corporation, are mixed together with 1000 grams of high density polyethylene at a speed of 175–200 rpm for 30 seconds after flux. The fluxed, pigmented resin is chopped up while warm and malleable, and then fed through a granulator. The resulting granules are molded on an injection molder with a 5 minute dwell time and a 30 second cycle time at a temperature of 200° C.

In Example 2 and Example 5, heat stability data is obtained by: heating colored plastic chips for 5 minutes at 20° C. temperature intervals from 200–300° C., then measuring the color change in the plastic chips using a CM-3600d spectrophotometer. As the temperature increases, a lower color difference (measured as dE in both masstone and tint) indicates better heat stability of the pigment used in coloring the plastics.

Definitions

[1] JONCRYL HPD-96 Styrene-acrylic copolymer. Molecular weight range of 8,500–16,500, acid number 215–240. Manufactured by SC Johnson Polymers, 8310 16th Street, P.O. Box 902, Sturtevant, Wis.
[2] SURFYNOL DF-37 Acetylenic defoamer. Manufactured by Air Products, 7201 Hamilton Boulevard, Allentown, Pa.
[3] SUNFAST 228-6725-2,9-dichloroquinacridone made by Sun Chemicals.
[4] Ciba CINQUASIA Magenta RT-265-D—Ciba commercial product, 2,9-dichloroquinacridone pigment.
[5] QUINDO Red R-6700—Commercial product, manufactured by Bayer Corporation.
[6] Ciba CINQUASIA Red RT-790-D—Ciba commercial product, gamma-quinacridone pigment.
[7] Ciba CINQUASIA Red NRT-742-D—Ciba commercial product, gamma-quinacridone pigment.
[8] Ciba CINQUASIA Red B NRT-796-D—Ciba commercial product, gamma-quinacridone pigment.
[9] Ciba CINQUASIA Violet R NRT-201-D—Ciba commercial product, beta-quinacridone pigment.
[10] Ciba CINQUASIA Violet R RT-791-D—Ciba commercial product, beta-quinacridone pigment.
[11] Ciba CINQUASIA Red Y RT-759-D—Ciba commercial product, gamma-quinacridone pigment.
[12] $ZrO_2/SiO_2$ beads are manufactured by Glen Mills Inc., 395 Allwood Road, Clifton, N.J., 07012.

Example 1

Crude 2,9-dichloroquinacridone Aqueous Milling

To a 4000 ml plastic beaker is added 858.4 g of 2,9-dichloroquinacridone press cake (46.6 wt. % solid), 391.6 g of water, 37.5 g of JONCRYL HPD-96[1] (34 wt. % solid), and 3.9 g of SURFYNOL DF-37[2] Defoamer. The above ingredients are mixed with a high shear stirrer (eg. a Ross Mixer) at a suitable setting for 5 minutes. The pH is adjusted to a range of 8.5–9.0 with 10% ammonium hydroxide. The resulting slurry is milled in the Dyno-mill.

The Dyno-Mill is filled with 1220 g (500 ml) of 1.0–1.25 mm $ZrO_2/SiO_2$ beads (mill gap setting at 0.10, tip speed 30 m/minute). The prepared pigment slurry is transferred to the Dyno-Mill until color comes out of the discharge tube. Milling is started at a flow rate of 80~100 ml/minute. Addition of JONCRYL HPD-96 and DF-37 are made as the milling continues in order to maintain fluid viscosity with a total of 45.5 g JONCRYL HPD-96 and 5.1 g of SURFYNOL DF-37 used. Sampling is made each hour in order to monitor the milling process. Total milling time is 4.8 hr, 42 passes are completed, and 1200 ml slurry product of 30.2 wt. % solid is obtained that is used for the ripening experiment in Example 2. Milled product shows higher chroma in both tint and masstone, and tint strength increases by 87% in comparison to the crude pre-milled pigment.

Example 2

Particle Size Re-Grow Process Suitable for Production of High Performance Opaque Pigment after Aqueous-Milling To a 1000 ml flask is added 120 ml of water, 24.0 g of NaOH (50% solution), 3.6 g 50% solution of benzyl tributylammonium chloride in hexylene glycol/water, and 7.2 g of pentanol, and stirred at room temperature for 10 minutes. 60 g slurry sample of Example 1 of the milled quinacridone is added to above mixture with stirring at room temperature for 30 minutes, then heating to reflux (97° C.) for 4 hr.

The reaction mixture is cooled to 60° C., transferred to a filtration funnel, filtered and washed with 0.1% aqueous sulfuric acid, then washed with hot water to a pH of 7.0. 22.9 g of 75.2 wt. % solid presscake sample are obtained. This sample is dried at 80° C. in an oven overnight, blended to the powder form, and submitted for paint and plastics screening.

Example 2 is tested in base coat/clear coat paint using SUNFAST Magenta 228-6725[3] commercial product as standard. Example 2 shows similar opacity, equal chroma in both masstone and tint, and bluer hue in masstone, with dE=0.5 in tint.

Plastic PVC test shows similar trend with dE=0.7 in tint. This data shows that Example 2 has similar color shade and performance to SUNFAST Magenta 228-6725[3] in both paint and plastic applications.

A heat stability test is performed using engineering plastics ABS media and Ciba commercial product CINQUASIA MAGENTA RT-265-D[4] as standard. The pigmented ABS is tested for heat stability in temperature ranges from 200° C. to 300° C. Example 2 is more heat stable than RT-265-D in both tint and masstone, with masstone dE=2 compared with masstone dE=2.87 for RT 265-D in the 200–300° C. temperature range.

Example 3

Crude Gamma Quinacridone and 2,9-dichloroquinacridone Mixture Aqueous-Milling

To a 4000 ml plastic beaker is added 972.7 g of gamma-quinacridone presscake (40.3 wt. % solid), 17.2 g of 2,9-dichloroquinacridone presscake (46.6 wt. % solid), 260.1 g of water, 47.0 g of JONCRYL HPD-96 (34 wt. % solid), and 9.0 g of SURFYNOL DF-37 defoamer. The above ingredients are mixed with a high shear stirrer (eg. a Ross Mixer) at a suitable setting for 15 minutes. The pH is adjusted to a range of 8.5–9.0 with 10% ammonium hydroxide. The resulting slurry is milled in the Dyno-Mill.

The Dyno-Mill is filled with 1220 g (500 ml) of 0.4–0.6 mm $ZrO_2/SiO_2$ beads (mill gap setting at 0.10, tip speed 30 m/minute). The pigment slurry is transferred to the Dyno-Mill until color comes out of the discharge tube. The milling is started at a flow rate of 80~100 ml/minute. Total milling time is 2.5 hr, 20 milling cycles are completed, and 1300 ml pigment slurry of 31.5 wt. % solids is obtained. The slurry sample is used for pre-laboratory test using Latex paint card drawdown method.

Example 4

Isolation of Example 3 After Aqueous-Milling

To 500 ml of Example 3 is added 2500 ml of water and pH is adjusted to 5.0–6.0 with 2% $H_2SO_4$. Sample is filtered and washed to pH=7.0. Continued vacuum filtration increases the solids to 47 wt. %. Example 4 is tested in a Latex paint system using Bayer R-6700[5] as standard. Example 4 shows same color space as QUINDO Red R-6700[5] with masstone dE=0.3 and tint dE=0.9.

Example 5

Sample Preparation for Example 3 to be Tested in Paint and Plastics

To a 2000 ml beaker is added 100 g of slurry in Example 3 (28.8 wt. % solid) and 1500 ml of water. The mixture is pH adjusted to 5.0 with 2% $H_2SO_4$. The slurry is filtered and washed with water. The press cake is dried at 80° C. overnight obtaining 24 g of sample. The sample is then Retsch milled to fine powder for testing in paint and plastic applications.

In the PVC test, Example 5 shows 11% higher tint strength than Ciba commercial product CINQUASIA RED B RT-790-D[6] with similar color shade and a dE<2.0 in both masstone and tint color. In engineering plastic HDPE (high density polyethylene), Example 5 also shows similar color to RT-790-D, with much better heat stability. While temperature increases from 200° C. to 300° C., dE of Example 5 in both masstone and tint is less than 1.5, compared to RT-790-D with dE=9.92 in masstone, and dE=12.1 in tint.

In base coat clear coat paint, Example 5 is compared with Ciba commercial products CINQUASIA RED B NRT-742-D[7] and CINQUASIA RED B NRT-796-D[8]. Results show Example 5 is more transparent than both standards, similar in color shade with tint/masstone dE<1.5, and metallic dE=2.0 compared to RT-796-D. In latex decorative paint application, Example 5 has higher strength than RT-796-D in both deep and light tones, similar color shade and slightly higher in chroma.

Example 6

Crude Beta-Quinacridone Aqueous Milling

To a 4000 ml plastic beaker is added 770.7 g of beta-quinacridone presscake (51.9 wt. % solid), 479.3 g of water, 37.5 g of JONCRYL HPD-96 (34 wt. % solid), and 3.9 g of SURFYNOL DF-37 defoamer. The above ingredients are Ross mixed at a setting of 5 for 15 minutes. The pH is adjusted to a range of 8.5–9.0 with 10% ammonium hydroxide to prepare slurry for milling in the Dyno-mill.

The Dyno-Mill is filled with 1220 g (500 ml) of 0.4–0.6 mm $ZrO_2/SiO_2$ beads (mill gap setting at 0.10, tip speed 30 m/minute). The pigment slurry is transferred to the Dyno-Mill until color comes out of the discharge tube with a starting mill flow rate of 80~100 ml/minute. Addition of JONCRYL HPD-96 and DF-37 are made as the milling continues in order to maintain the fluidity with a total of 111.5 g JONCRYL HPD-96 and 6.9 g of DF-37 used. Sampling is made each hour in order to monitor the milling process. Total milling time is 12.3 hr, 96 milling cycles are completed, and 1200 ml slurry product of 32.0 wt. % solid is obtained. The slurry product is pH adjusted to ~5.0, filtered and washed with hot water to pH~7.0. The press cake sample is dried at 80° C. in an oven overnight, then Retsch milled to a fine powder for paint and plastic screening.

The product of Example 6 is compared with Ciba commercial product CINQUASIA VIOLET R NRT-201-D[9] in base coat/clear coat paint, and shows a similar color shade to NRT-201-D with dE=0.4 in tint. It is more transparent than NRT-201-D in masstone, and slightly yellower in metallic color.

Example 6 is also compared with Ciba commercial product CINQUASIA VIOLET-R RT-791-D[10] in PVC plastics. Compared with RT-791-D, Example 6 is identical in tint color with higher tint strength, and higher chroma than RT-791-D in masstone with dE=3.5.

Example 7

Example 6 is repeated except that 0.3–0.4 mm $ZrO_2/SiO_2$ beads are used in the milling process, and experiment is stopped at 8 hour. A product similar to Example 6 is obtained.

Example 8

Crude Gamma-Quinacridone Aqueous Milling

To a 4000 ml plastic beaker is added 992.6 g of gamma-quinacridone presscake (40.3 wt. % solid), 386.1 g of water, 48.8 g of JONCRYL HPD-96 (34 wt. % solid), and 3.9 g of SURFYNOL DF-37 Defoamer. The above ingredients are Ross mixed at a setting of 5 for 15 minutes. The pH is adjusted to 9.4 with 10% ammonium hydroxide and the prepared slurry is milled in the Dyno-mill.

The Dyno-Mill is filled with 1220 g (500 ml) of 0.4–0.6 mm $ZrO_2/SiO_2$ beads (mill gap setting at 0.10, tip speed 30 m/minute). The prepared pigment slurry is transferred to the Dyno-Mill until color comes out of the discharge tube. Milling is started at a flow rate of 80~100 ml/minute. Addition of JONCRYL HPD-96 and DF-37 are made as the milling continues in order to maintain fluidity, total of 64.8 g JONCRYL HPD-96 and 7.8 g of DF-37 is used. Sampling is made each hour in order to monitor milling process. Total milling time is 5 hr. 1300 ml product with 25.6 wt. % solid content is obtained. Although starting gamma-quinacridone has gamma-II phase, as milling continues, the crystals change phase to gamma-I. The final product has 100% gamma-I crystal phase with a bluer tint color, more transparent, and higher chroma in both tint and masstone color than the starting pigment Ciba CINQUASIA Red Y RT-759-D[11].

Example 9

Crude Perylene Aqueous Milling

To a 4000 ml plastic beaker is added 1295.3 of perylene (Lot # MO2326D) presscake (38.6 wt. % solid), 434.2 g of water, 73.5 g of JONCRYL HPD-96 (34 wt. % solid), and 5.0 g of SURFYNOL DF-37 Defoamer. The above ingredients are mixed with a high shear stirrer for 15 minutes. The pH is adjusted to 9.4 with 10% ammonium hydroxide and the prepared slurry is milled in the Dyno-mill.

The Dyno-Mill is filled with 1170 g of 0.4–0.6 mm $ZrO_2/SiO_2$ beads (Mill Gap setting at 0.10, tip speed 30M/minute). The prepared pigment slurry is transferred to Dyno-Mill until color comes out of the discharge tube. Milling is started at a flow rate of 80~100 ml/minute. Addition of JONCRYL HPD-96 and DF-37 are made as the milling continues in order to maintain fluidity, a total of 238.2 g JONCRYL HPD-96 (34 wt. % active ingredients) and 7.0 g of DF-37 is used. Sampling is made each hour in order to monitor milling process. Total milling time is 5 hr. 1300 ml pigment slurry with a 25.7 wt. % solid content is obtained.

Comparison of wet-milled crudes with the starting crude in a latex paint system

| Sample | % Strength Tint | *DC*, Masstone |
|---|---|---|
| 2,9-dichloroquinacridone crude (Control) | 100.00 | 0.00 |
| Example 1 | 187.10 | 0.14 |
| gamma quinacridone and 2,9-dichloro-quinacridone crude mix (Control) | 100.00 | 0.00 |
| Example 3 | 115.25 | 2.35 |
| beta-quinacridone crude (Control) | 100.00 | 0.00 |
| Example 6 | 164.33 | -3.87 |
| beta-quinacridone crude (Control) | 100.00 | 0.00 |
| Example 7 | 166.93 | -1.22 |
| gamma-quinacridone crude (Control) | 100.00 | 0.00 |
| Example 8 | 127.64 | 2.26 |
| Perylene crude (Control) | 100.00 | 0.00 |
| Example 9 | 123.60 | 2.29 |

Latex Paint Formulation:

Deep Base—PREMIUM PLUS Interior Semi-Gloss Enamel, #5340, 100% acrylic latex. BEHR Process Corporation, 3400 W. Segerstrom Ave., Santa Ana, Calif. 92704.

Pastel Base—PREMIUM PLUS Interior Semi-Gloss Enamel, #5560, 100% acrylic latex. BEHR Process Corporation, 3400 W. Segerstrom Ave., Santa Ana, Calif. 92704.

Masstone sample is made by mixing 2.5 g (30 wt. % pigment loading in water) milled slurry product with 47.5 g of Deep Base carrier.

Tint sample is made by mixing 0.6 g (30 wt. % pigment loading in water) of milled slurry sample with 50 g of Pastel Base carrier.

*DC, chroma change.

We claim:

1. A process for particle size reduction of organic pigments to improve the optical properties of pigments wherein the process comprises
   (a) milling
   a mixture comprising:
      i.) from about 10 to about 60 wt. % of one or more crude organic pigments,
      ii.) from about 0.1 to about 25 wt. % of water soluble styrene copolymer dispersant based on the dry weight of the crude organic pigment,
      iii.) optionally from about 0.1 to about 1.0 wt. % of a defoamer,
      iv.) optionally from about 0.1 to about 5.0 wt. % of an additive based on the dry weight of the crude organic pigment, and
      v.) greater than about 10 wt. % water
   wherein components i.), iii.), and v.) weights are based on the total weight of the mixture, and
   (b) isolating the organic pigment.

2. A process according to claim 1 wherein the crude organic pigment is selected from the group consisting of perylenes, quinacridones, phthalocyanines, isoindolines, dioxazines, triphendioxazines, 1,4-diketopyrrolopyrroles, anthrapyrimidines, anthranthrones, flavanthrones, indanthrones, perinones, pyranthrones, thioindigos, 4,4'-diamino-1,1-dianthraquinonyl, and azo compounds, substituted derivatives and mixtures thereof.

3. A process according to claim 1 wherein the crude organic pigment is perylene, quinacridone, phthalocyanine, isoindoline, 1,4-diketopyrrolopyrroles or dioxazine pigments.

4. A process according to claim 1 wherein the crude organic pigment is a quinacridone of formula (A) or mixture of different derivatives of formula (A)

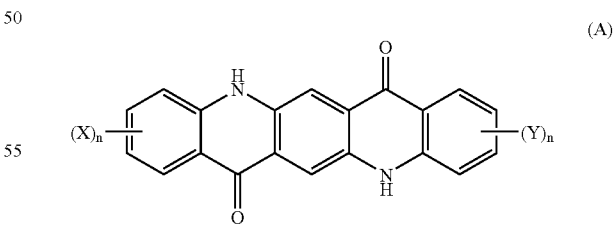

in which X and Y, independently of one another, are halogen, —OH, —$NO_2$, —$CF_3$, a $C_1$–$C_4$alkyl group, a substituted $C_1$–$C_4$alkyl group, a $C_1$–$C_4$alkoxy group, a substituted $C_1$–$C_4$alkoxy group, a phenyl group, a cyclohexyl group, a phenoxy group, —COOH, a —COO—$C_1$–$C_4$alkyl group, —$SO_3H$, a phenylamino group, a benzamino group, —$N(CH_3)_2$, —$SO_2NH_2$, —$SO_2N(CH_3)_2$, a pyridino group, —$CONH_2$ or —$CON(CH_3)_2$, and n is 0, 1, or 2.

5. A process according to claim 4 wherein the quinacridone is unsubstituted quinacridone, 2,9-dichloroquinacridone, 3,10-dichloroquinacridone, 4,11-dichloroquinacridone, 2,3,9,10-tetrachloroquinacridone, 2,4,9,11-tetrachloroquinacridone, 2,9-difluoroquinacridone, 2,9-dibromoquinacridone, 2,9-dimethylquinacridone, 3,10-dimethylquinacridone, 4,11-dimethylquinacridone, 2,4,9,11-tetramethylquinacridone, 2,9-di(tert-butyl)quinacridone, 2,9-dihydroxylquinacridone, 2,9-di(trifluoromethyl)quinacridone, 2,9-dimethoxyquinacridone, 2,9-diethoxyquinacridone, 2,4,9,11-tetramethoxyquinacridone, 2,9-dicarboxylquinacridone, 2,9-dichlorohexylquinacridone, 2,9-diphenylquinacridone, 2,9-di(dimethylamino)quinacridone, 2,9-di(dimethylaminosulfo)quinacridone, 2,9-di(dimethylaminocarbonyl)quinacridone, 3,10-dinitroquinacridone, 2,9-dimethyl-4,11-dichloroquinacridone, 2,9-dimethyl-4,11-dicarboxyquinacridone, or 2,9-dipyridinoquinacridone of beta or gamma crystal phase.

6. A process according to claim 4 wherein the quinacridone is an unsubstituted beta or gamma quinacridone or 2,9-dichloroquinacridone.

7. A process according to claim 1 wherein the styrene copolymer dispersant has a chemical structure shown in formula (B)

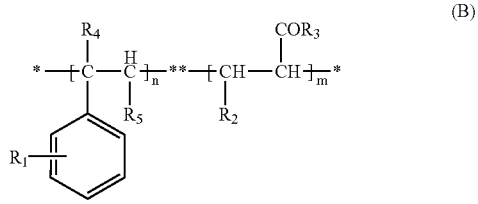

where $R_1$ is H, $C_1$–$C_4$ alkyl, fluoro, chloro, bromo, iodo, nitro, or amino groups, $C_1$–$C_{18}$ alkylene, or $C_1$–$C_4$ alkoxy groups; $R_2$ is H and $C_1$–$C_4$ alkyl group, $R_3$ is hydroxyl or $C_{1-4}$ alkoxy group, and 100>n>1, 100>m>1; and $R_4$ and $R_5$ are independently of one another, H, or $C_1$–$C_4$ alkyl group.
* is an endcapping unit or terminating group and
** shows that the copolymer may be random, block or grafted.

8. A process according to claim 7 wherein the styrene copolymer dispersant is a random, block or graft copolymer.

9. A process according to claim 7 wherein the styrene copolymer dispersant has a molar ratio of styrene to (meth)acrylic monomer units that is equal to or greater than about 2 to 1.

10. A process according to claim 7 wherein the styrene copolymer dispersant comprises a maximum of about 49% (meth)acrylic acid, (meth)acrylic acid derived monomer units or salts thereof, based on the total number monomer units of the copolymer dispersant.

11. A process according to claim 7 wherein the styrene copolymer dispersant has a molecular weight range of about 5,000 to about 20,000.

12. A process according to claim 11 wherein the styrene copolymer dispersant has a molecular weight range from about 9,000 to about 17,000.

13. A process according claim 1 wherein the one or more crude organic pigments component (i) has a particle size range of about 0.3 to about 4.0 μm.

14. A process according to claim 1 wherein the isolated milled pigment or the milled mixture composition has a particle size range of about 30 to about 300 nm.

15. A process according to claim 1 wherein the isolated milled organic pigment or the milled mixture composition is re-grown under basic conditions to form an opaque pigment.

16. A process according to claim 1 wherein the percent weight of water of component (v) is greater than about 30 wt. %.

17. A process according to claim 1 wherein the percent weight of pigment in component (i) is about 20 to about 45 wt. %.

18. A pigment composition obtained according to the process of claim 1, wherein the crude pigment is a beta or gamma quinacridone.

19. A coating composition containing a pigment obtained according to claim 1, wherein the crude pigment is a beta or gamma quinacridone.

20. A high molecular weight organic material having incorporated therein the organic pigment obtained according to claim 1, wherein the high molecular weight organic material is defined as material in the range of $10^3$ to $10^8$ g/mol and the crude pigment is a beta or gamma quinacridone.

21. A material according to claim 20, wherein the material is an ink, coating or plastic.

22. A material according to claim 21, wherein the plastic is a film, fiber or molded article.

23. A process for coloring a high molecular weight organic material, which comprises incorporating an effective pigmenting amount of the organic pigment according to claim 1 into the high molecular weight organic material, wherein high molecular weight organic material is defined as material in the range of $10^3$ to $10^8$ g/mol and the crude pigment is a beta or gamma quinacridone.

* * * * *